United States Patent [19]
Jabba

[11] Patent Number: 5,421,334
[45] Date of Patent: Jun. 6, 1995

[54] PRE-FILLED IMAGING CATHETER

[75] Inventor: Ronald J. Jabba, Los Altos Hills, Calif.

[73] Assignee: Cardiovascular Imaging Systems, Inc., Sunnyvale, Calif.

[21] Appl. No.: 132,371

[22] Filed: Oct. 6, 1993

[51] Int. Cl.6 ............................................. A61B 8/12
[52] U.S. Cl. .................................................. 128/662
[58] Field of Search ........... 128/660.03, 660.1, 662.06; 604/96–103, 132, 136

[56] References Cited

U.S. PATENT DOCUMENTS

| | | | |
|---|---|---|---|
| 3,880,163 | 4/1975 | Ritterskamp | 604/136 |
| 3,993,069 | 11/1976 | Buchler et al. | 604/132 |
| 4,375,818 | 3/1983 | Suwaki et al. | 128/662.06 |
| 4,794,931 | 1/1989 | Yock | 128/660 |
| 4,951,677 | 8/1990 | Crowley et al. | 128/662.06 |
| 5,000,185 | 3/1991 | Yock | 128/662.06 |
| 5,002,059 | 3/1991 | Crowley et al. | 128/662 |
| 5,049,130 | 9/1991 | Powell | 604/96 |
| 5,117,831 | 6/1992 | Jang et al. | 128/662 |
| 5,121,749 | 6/1992 | Nassi et al. | 128/662.06 X |
| 5,190,046 | 3/1993 | Shturman | 128/662.06 |

Primary Examiner—Francis Jaworski
Attorney, Agent, or Firm—Townsend and Townsend Khourie and Crew

[57] ABSTRACT

The present invention provides an improved imaging catheter which is pre-filled with a fluid suitable for the transmission of imaging signals. Such a catheter eliminates the need for the user to fill and flush the catheter with fluid prior to its use. A catheter according to the present invention may be stored in a container which itself contains fluid to prevent fluid loss. Some embodiments will include reservoirs to hold a supply of fluid to replace that lost, for example, to evaporation. In some embodiments, these reservoirs will further include means for applying pressure to the fluid contained therein so that new fluid is forced into the catheter to replace any fluid lost.

16 Claims, 5 Drawing Sheets

PRE-FILLED IMAGING CATHETER

BACKGROUND OF THE INVENTION

1. Field of the Invention

The present invention provides an improved catheter for imaging structures within the body of a patient. More particularly, the present invention provides an imaging catheter which is pre-filled with a fluid suitable for the transmission of imaging energy. The improved catheter may also include a reservoir to hold a supply of fluid to replace fluid lost by evaporation and vapor transmission through the catheter material.

2. Description of the Background Art

Methods and apparatus for imaging structures within the body of a patient are described in U.S. Pat. Nos. 4,794,931 and 5,000,185 to Yock, U.S. Pat. No. 5,117,831 to Jang et al., and elsewhere. Imaging catheters of the type described include a transducer, typically an ultrasonic transducer, at the distal end of a flexible tubular member which constitutes the catheter body.

Ultrasonic energy produced by the transducer is readily transmitted by water or saline solution, as well as blood and other body fluids. Ultrasonic energy is not readily transmitted by air however. Therefore, any air present in the catheter in the region of the transducer must ordinarily be flushed out of the catheter prior to its use. Saline solution or sterile water is typically used for this purpose. The fluid flush must be sufficiently vigorous and thorough to ensure the removal of all air from the catheter. Even a very small bubble in the region of the transducer may prevent satisfactory imaging.

An imaging catheter of the type described is commonly furnished with a flush port or other opening at its proximal end through which fluid may be injected to accomplish the desired flush. This configuration is less than ideal for flushing air from the distal end however. The narrow distal tip makes it difficult to adequately flush the interior of the catheter to eliminate air bubbles at the distal tip in the vicinity of the ultrasonic transducer.

An alternative approach to flushing the catheter is described in U.S. Pat. No. 5,049,130 to Powell, the disclosure of which is incorporated herein by reference. The Powell patent discloses an imaging catheter having a port near its proximal end for injecting flushing fluid into the catheter. The distal end is equipped with a special sheath.

Normally, the sheath disclosed in the '130 patent closes off and seals the distal end of the catheter. The sheath is composed of an elastic material, however, which allows it to deform in response to internal pressure within the catheter. When fluid is injected into the proximal end of the catheter, the sheath deforms in response and a flow path opens through the sheath at the distal end of the catheter. Air within the catheter may thereby be flushed out of the distal end of the catheter through the sheath.

An alternate approach to achieving adequate flushing of the region around the transducer is disclosed in U.S. Pat. No. 5,002,059 to Crowley et al. This patent describes an imaging catheter in which the transducer is housed within a chamber at the distal end of the catheter. The chamber has a cylindrical plug formed of a silicone elastomer or equivalent polymer. A syringe needle may be inserted into the chamber through the plug so that fluid may be injected directly into the region housing the transducer.

Each of the catheters described above is less than ideal in that the physician is required to flush the catheter prior to its use. This procedure can be time consuming and it is often difficult to ensure that the catheter has been flushed sufficiently to remove all air from the vicinity of the transducer.

It would be desirable therefore to provide a catheter pre-filled with saline solution or another fluid suitable for the transmission of ultrasound or other imaging signals. It would further be desirable if such a catheter were provided with a reservoir to hold a supply of the fluid to replace fluid lost from the catheter, e.g., through evaporation. This would allow the storage of the catheter for extended periods prior to its use. It would further be desirable if the catheter were provided with means for applying pressure to force fluid from the reservoir into the catheter in the event fluid is lost from the catheter.

SUMMARY OF THE INVENTION

The present invention comprises an improved imaging catheter which is pre-filled with a fluid suitable for the transmission of imaging signals. A catheter according to the present invention is superior to conventional imaging catheters in that the physician is not required to flush the catheter of air prior to use. The improved catheter is prepared more quickly and is therefore more convenient to use. The prefilled catheter is further advantageous in that it substantially eliminates uncertainty as to whether air, which would interfere with imaging, is present in the vicinity of the imaging element.

Preferred embodiments of pre-filled catheters according to the present invention will have reservoirs for holding a supply of fluid to replace fluid lost from the catheter. Some embodiments will include means for applying pressure to the fluid in the reservoir so that fluid will be forced into the catheter if fluid is lost. Pressure may be applied to the fluid by using an elastic bladder as the reservoir or by holding the fluid in a syringe provided with a spring to urge the plunger into the barrel of the syringe.

DESCRIPTION OF SPECIFIC EMBODIMENTS

Figure 1:
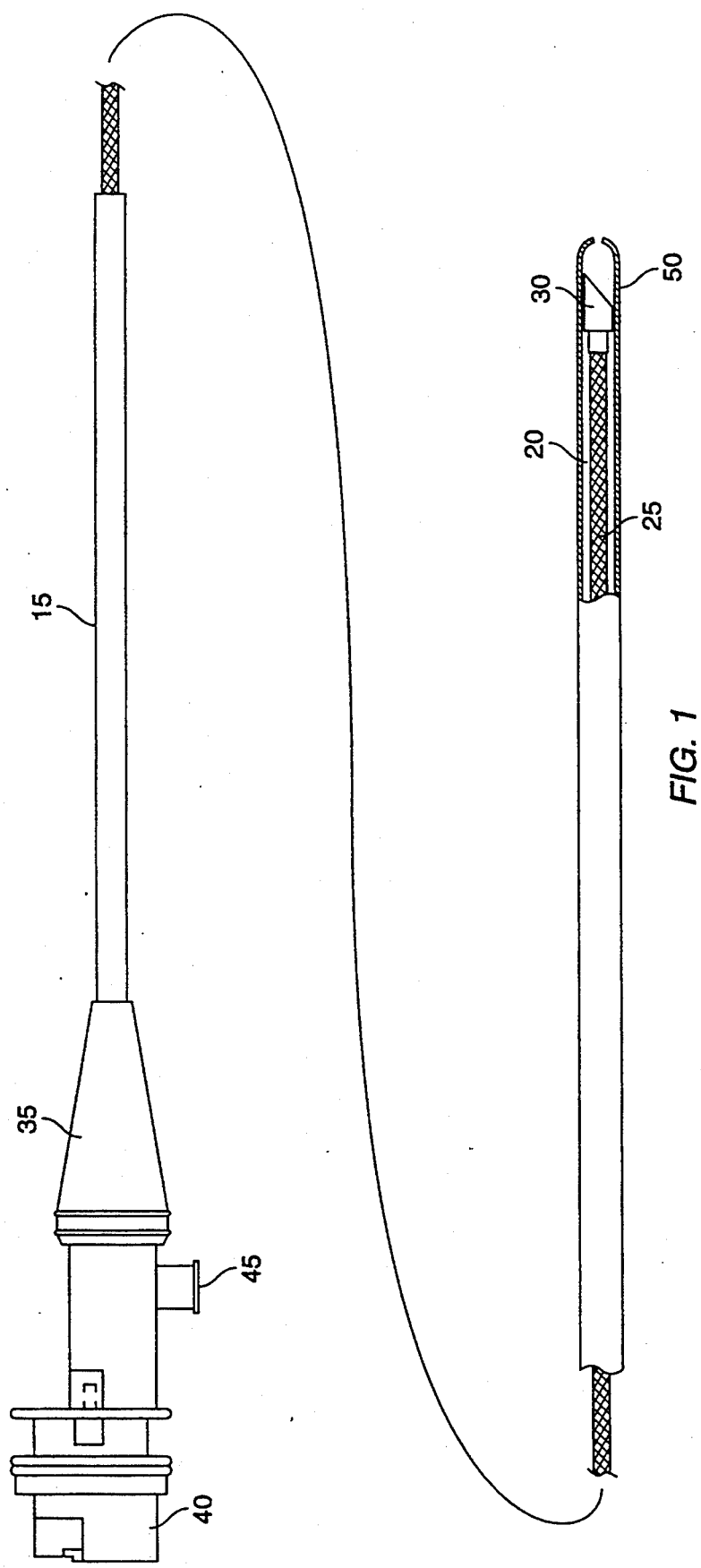
FIG. 1 depicts an imaging catheter that must be filled with fluid and flushed of air prior to its use.

FIG. 1 depicts an imaging catheter of the type requiring a conventional fill and flush procedure. The catheter depicted comprises a flexible catheter body with an inner lumen 20 running therethrough. A drive cable 25 is disposed within the lumen. An ultrasonic transducer 30 is connected to the distal end of the drive cable so that the transducer rotates in response to rotation of the drive cable.

The particular catheter depicted includes a proximal end assembly 35, which includes an end connection 40 for connecting the drive cable to an external drive motor (not shown). The proximal end assembly further includes a flush port 45 in communication with inner lumen 20 of the catheter body.

Prior to inserting the catheter into the patient, the physician must inject a fluid suitable for the transmission of ultrasonic energy through the flush port to fill the inner lumen. The flushing must be sufficiently vigorous to ensure that no air remains trapped in the inner lumen at distal end 50 in the region of the transducer.

The need for the physician to fill and flush the catheter prior to using it is disadvantageous in that adds a step to the imaging procedure. The flushing process can be time consuming and in practice it is often difficult to ensure that no trapped air remains in the vicinity of the transducer. Air is a very poor conductor of ultrasonic energy; even a small bubble in the vicinity of the transducer may interfere substantially with imaging.

The catheter may advantageously be made pre-filled to eliminate the need for the physician to perform the filling and flushing operation. A pre-filled catheter according to the present invention will leave the factory with the inner lumen filled with a suitable fluid. Such a catheter will be sealed to minimize loss or evaporation of the fluid from the catheter. A catheter of this type can be of the same general configuration as that depicted in FIG. 1 except that flush port 45 will be sealed or eliminated entirely.

Complete prevention of fluid loss may be impractical. Because the inner volume of the lumen is very small, and because a given catheter may be stored for an extended period of time prior to use, even slight evaporation may be significant. For example, the external diameter of a catheter suitable for ultrasonic imaging of vascular occlusions may be between 2 and 10 French, or even smaller. Such a catheter might have an internal lumen with a diameter of between about 0.010 to 0.100 inches. A lumen of that diameter and 90 to 175 cm in length would have an internal volume of only about 1 to 10 milliliters. The actual volume of fluid within the lumen would be considerably less due to the presence of the drive shaft. Such a catheter would typically be stored for a number of months, and possibly longer, before being used.

Figure 2:
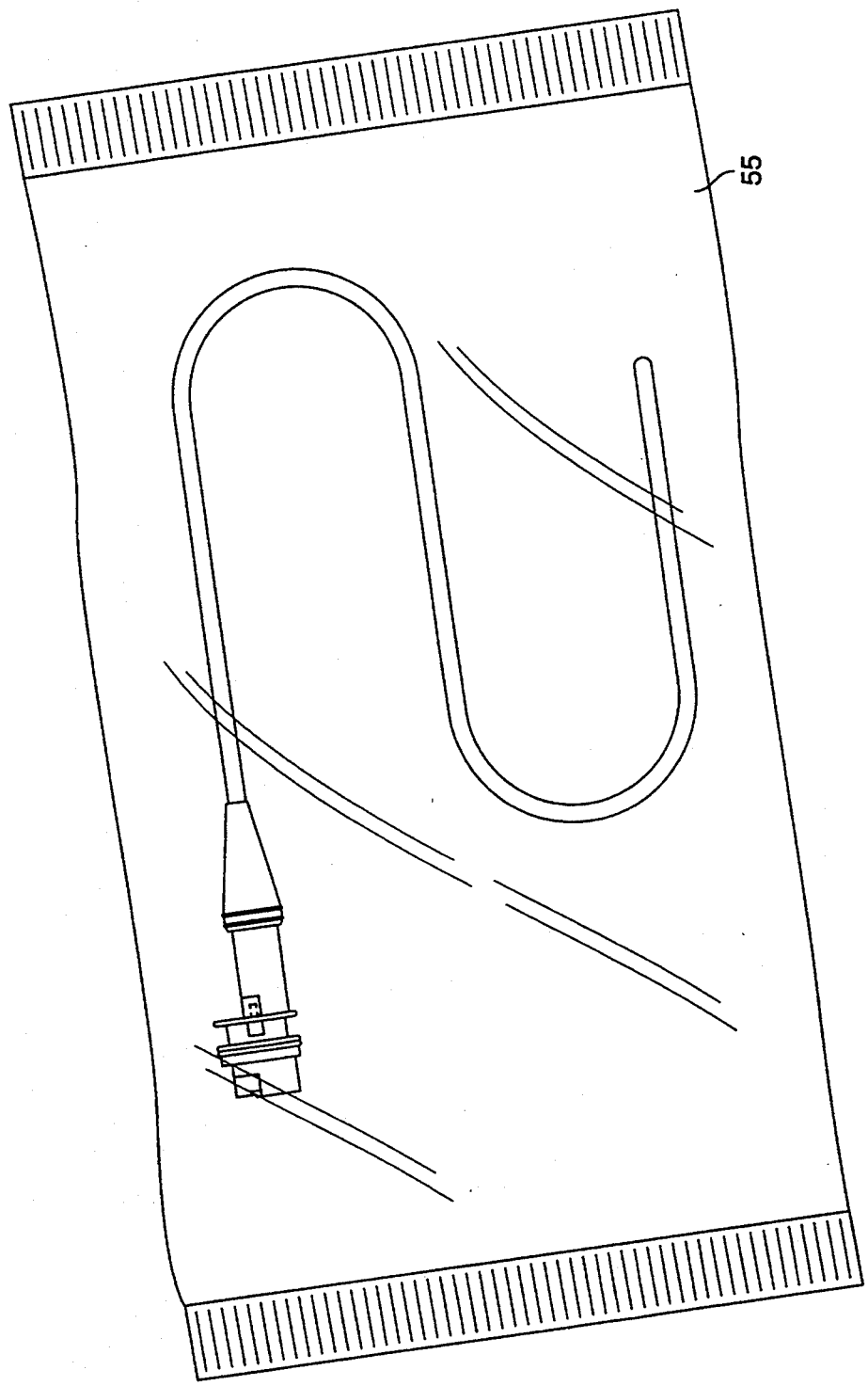
FIG. 2 depicts a pre-filled imaging catheter that does not need to be filled or flushed and which is packaged in a bag full of fluid to prevent fluid loss.

To address the problem of fluid loss during prolonged storage, a pre-filled catheter like that described may be packaged in a container in the form of a sealed bag 55, as depicted in FIG. 2. In this case, the bag itself is filled with a large volume of sterile saline solution or other suitable fluid. The bag is not opened until the physician is ready to use the catheter. The relatively large volume of fluid surrounding the catheter during storage eliminates any potential for evaporation of fluid from the catheter during extended storage. Note that in contrast to the catheter depicted in FIG. 1, the pre-filled catheter of FIG. 2 has no flush port.

Figure 3:
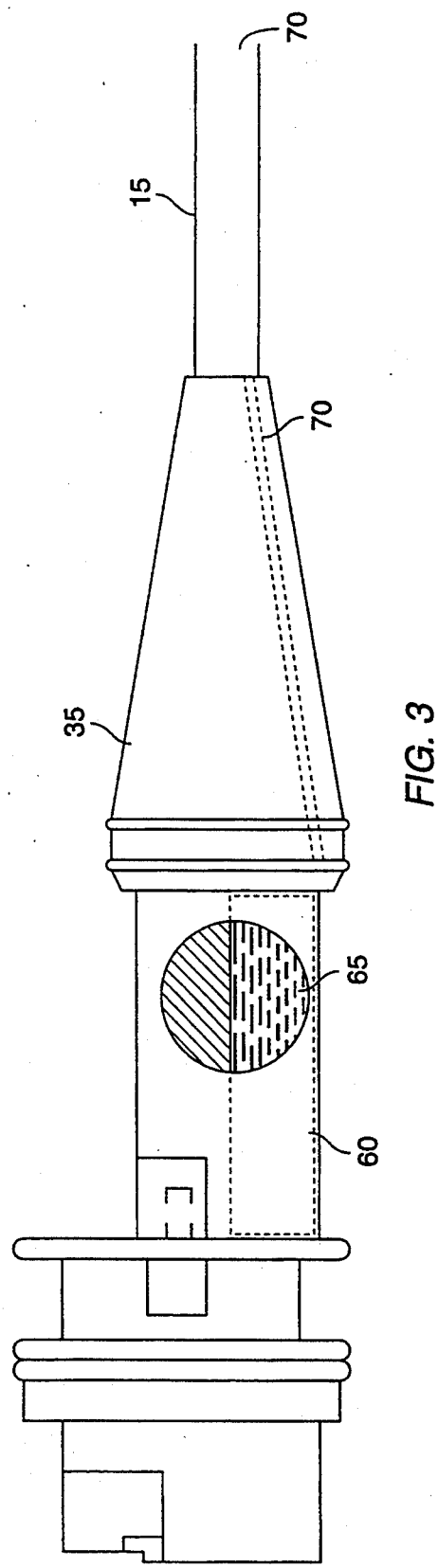
FIG. 3 is an illustration of the proximal end of a pre-filled catheter having an internal fluid reservoir to hold a supply of fluid suitable for imaging.

FIG. 3 depicts an alternative means for minimizing the effect of fluid loss or evaporation from the catheter. The catheter depicted has a proximal end assembly 35, which includes an internal fluid reservoir 60. The reservoir holds a supply of fluid 65 and is placed in communication with inner lumen 20 of the catheter through fluid channel 70.

The internal reservoir adds to the effective volume of the inner lumen and the fluid contained therein. This larger fluid volume means that loss of a given small amount of fluid through loss or evaporation constitutes a smaller portion of the total fluid within the catheter. If fluid is lost, the reservoir provides a supply of fluid to replace it. A reservoir incorporated into the proximal hub of the type depicted may contain at least approximately 50, and more preferably about 100, milliliters of fluid. The internal volume of the reservoir should preferably be at least about 5 times that of the lumen. However, the precise volume is obviously not critical to the practice of the present invention.

Figure 4:
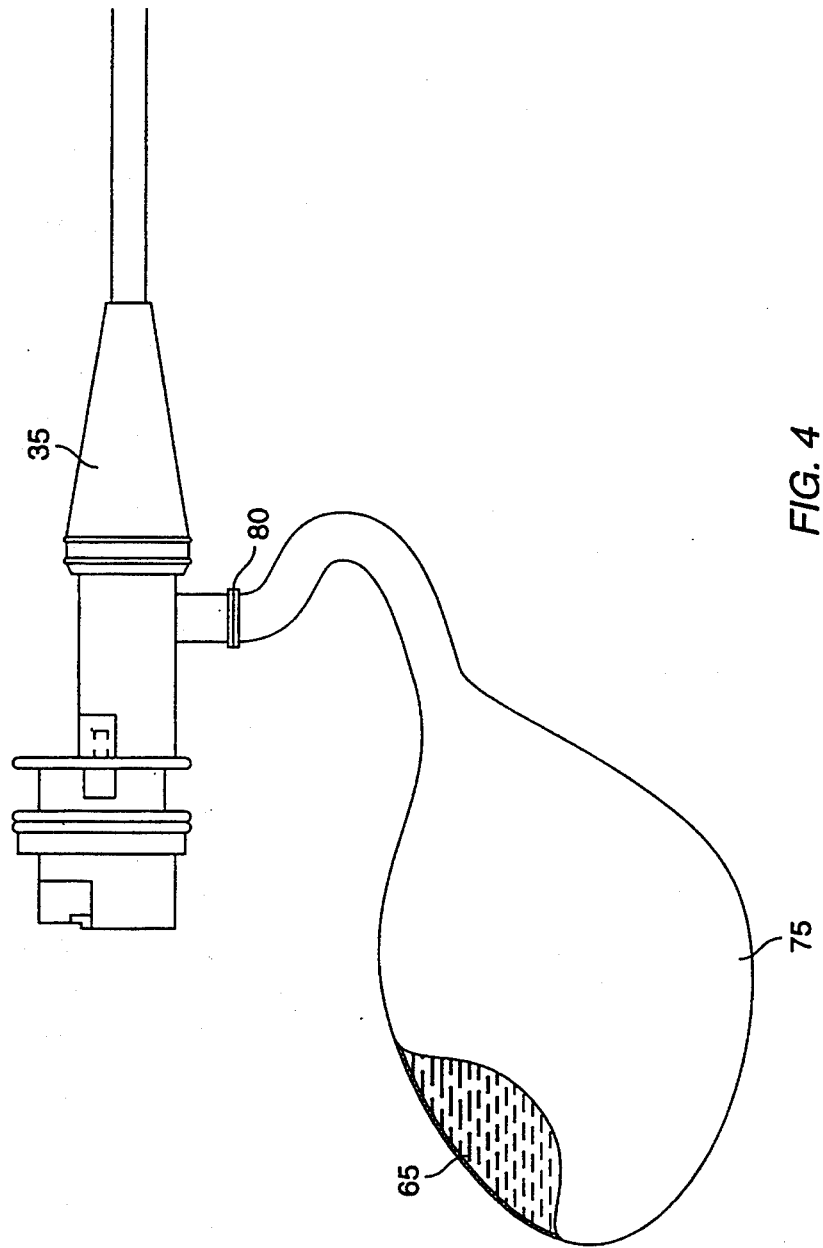
FIG. 4 depicts the proximal end of a pre-filled catheter with an external reservoir in the form of an elastic bladder, which holds and applies pressure to a suitable fluid contained therein.

An alternative embodiment for a pre-filled catheter having a fluid reservoir is depicted in FIG. 4. As can be seen therein, this catheter includes an external reservoir in the form of an elastic bladder 75, in which a volume of a suitable fluid 65 is contained. The bladder is in fluid communication with the lumen of the catheter through connection 80.

The bladder is made of an elastic material, which places a constrictive force on the fluid contained within it. This constrictive force applies pressure to the fluid. If fluid is lost from the lumen of the catheter, the pressure will force fluid out of the bladder and into the lumen to replace the fluid that was lost. An elastic bladder of the type depicted may conveniently be made to hold about 100 milliliters of fluid under a pressure of about 5 to 75 pounds per square inch.

Connection 80 may advantageously be made in the form of a "Luer lock," a connection commonly found on syringes and other medical equipment. A Luer lock provides a relatively secure but easily removable connection between the bladder and the catheter. It will ordinarily be desirable to remove the bladder from the catheter prior to use so that the bladder will not be dangling from the catheter as the physician performs the delicate task of threading the catheter body into and through the patient's vascular system. Alternatively, an elastic bladder could be permanently joined to the catheter and fixed more securely to the proximal end connection or the catheter body.

Figure 5:
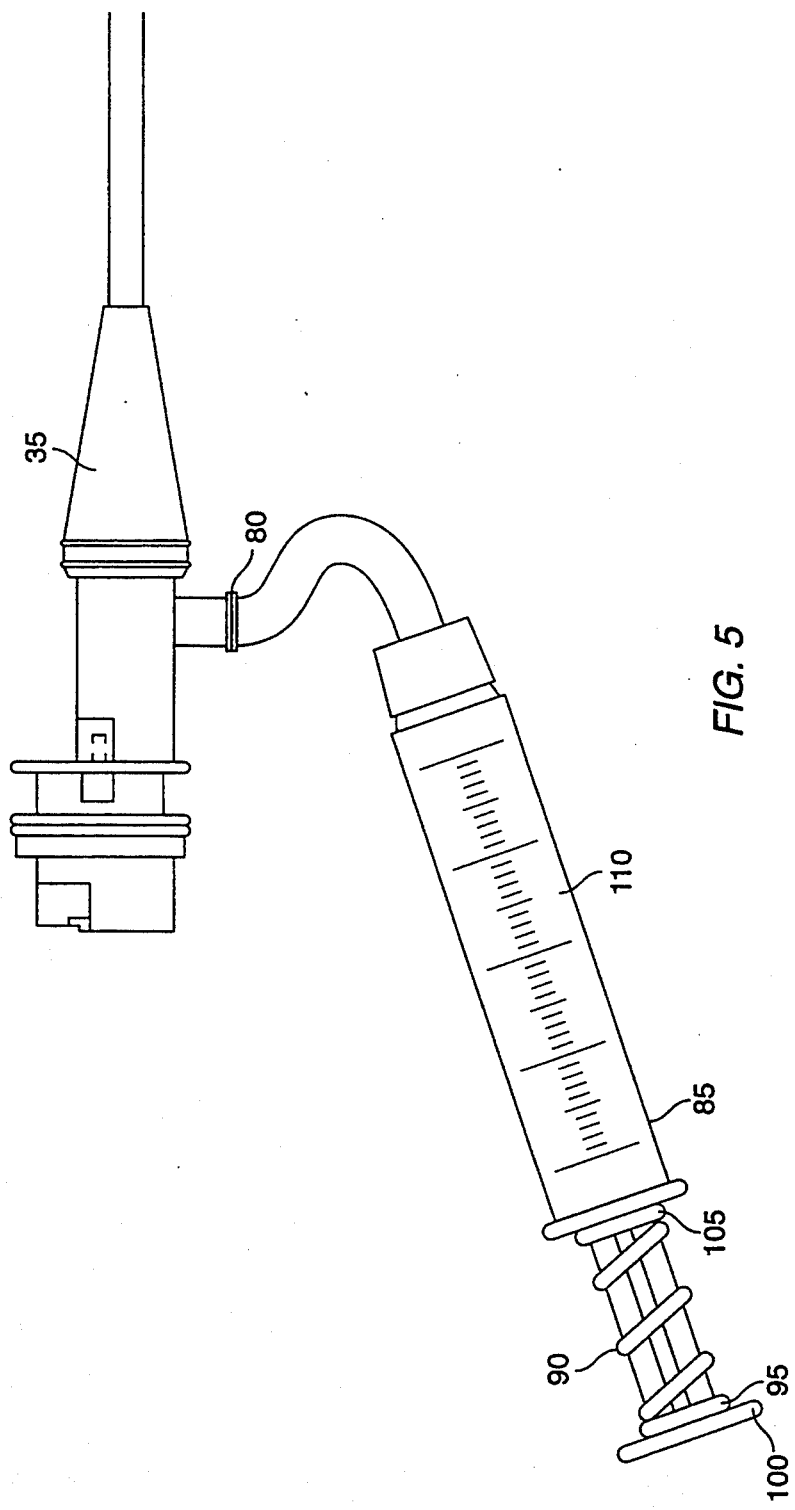
FIG. 5 is an illustration of the proximal end of a pre-filled catheter with an external reservoir in the form of a syringe, which has a spring to hold and apply pressure to the fluid contained therein.

An alternative external reservoir is depicted in FIG. 5, which shows a syringe 85 filled with a fluid suitable for imaging connected to the proximal end assembly of a pre-filled catheter. In the embodiment depicted, the syringe is provided with a helical spring 90. The spring is fixed at one end 95 to plunger 100 of the syringe and at the other end 105 to barrel 110, in which the fluid is held. The spring is installed on the syringe so that it is stretched beyond its unstressed length. The spring will therefore apply a compressive force which will tend to force the plunger of the syringe into the barrel.

This arrangement will function similarly to the elastic bladder depicted in FIG. 4. If fluid is lost from the catheter, the spring force will urge fluid out of the syringe and into the catheter to replace the fluid lost. The syringe of FIG. 5 is also similar to the bladder of FIG. 4 in that it may conveniently be removed from the catheter prior to its use. A syringe having a fluid volume of at least twenty milliliters will most often be used for this purpose.

What is claimed is:

1. An improved imaging catheter of the type comprising a flexible tubular catheter body having proximal and distal ends and a lumen therethrough; a drive shaft disposed within the lumen of the catheter body; and an imaging transducer connected to the drive shaft and disposed within the lumen at the distal end of the catheter body, wherein the improvement comprises:

a housing attached to the proximal end of the catheter body, the housing defining a fluid reservoir in communication with the lumen, the fluid reservoir having a volume greater than a volume of the lumen; and liquid contained within the lumen and the reservoir, the lumen and the reservoir being sealed to hold the liquid therein.

2. An improved imaging catheter of the type comprising a flexible tubular catheter body having proximal and distal ends and a lumen therethrough; a drive shaft disposed within the lumen of the catheter body; and an imaging transducer connected to the drive shaft and disposed within the lumen at the distal end of the catheter body, wherein the improvement comprises:

a fluid reservoir in communication with the lumen of the catheter body;

a supply of liquid contained within the reservoir and the lumen of the catheter body; and wherein the catheter body is continuously formed around the lumen at the distal end to seal the liquid within the lumen.

3. The improved catheter of claim 2, further comprising means for applying pressure to the liquid in the reservoir.

4. The improved catheter of claim 3, wherein the pressure applied to the liquid is between about 5–75 psi.

5. The improved catheter of claim 3, wherein the reservoir is an elastic bladder and wherein the pressure arises from elastic tension in the bladder.

6. The improved catheter of claim 3, wherein the reservoir comprises a syringe having a barrel and a plunger and wherein the pressure means comprises a spring which applies a force to urge the plunger into the barrel of the syringe.

7. The improved catheter of claim 2, wherein the reservoir is detachable from the catheter body.

8. The improved catheter of claim 7, wherein the reservoir is detachably connected to the catheter body by means of a Luer lock.

9. The improved catheter of claim 2, wherein the fluid reservoir contains at least twenty milliliters of liquid.

10. The improved catheter of claim 2, wherein the internal volume of the reservoir is at least five times the internal volume of the lumen.

11. An imaging catheter and packaging comprising:

an imaging catheter comprising a flexible tubular catheter body having proximal and distal ends and a lumen therethrough, a drive shaft disposed within the lumen of the catheter body, an imaging transducer connected to the drive shaft and disposed within the lumen at the distal end of the catheter body, and a liquid contained within the lumen;

a container within which the imaging catheter is held, the container further holding a supply of liquid which substantially surrounds the catheter.

12. The imaging catheter and packaging of claim 11, wherein the container is a sealed bag.

13. A method for storing a catheter, said method comprising:

providing a flexible tubular catheter body having proximal and distal ends and a lumen therethrough;

filling the lumen of the catheter with a liquid; and sealing the lumen of the catheter body in the presence of an excess amount of fluid.

14. The method of claim 13, wherein the lumen is sealed by sealing the catheter body in a container having a supply of liquid which substantially surrounds the catheter.

15. The method of claim 13, wherein the lumen is sealed by continuously forming the catheter body around the lumen at the distal end of the catheter body, and by attaching a housing to the proximal end of the catheter body, the housing defining a fluid reservoir in communication with the lumen.

16. The method of claim 13, wherein the lumen is sealed by placing a fluid reservoir in communication with the lumen of the catheter body, the fluid reservoir comprising an elastic bladder.

* * * * *